(12) United States Patent
Miranda et al.

(10) Patent No.: US 6,639,101 B2
(45) Date of Patent: Oct. 28, 2003

(54) ISOCYANATE PRODUCTION PROCEDURE

(75) Inventors: Sergio Castillon Miranda, Altafulla (ES); Carmen Claver Cabrero, Altafulla (ES); Elena Fernandez Gutierrez, Tarragona (ES); Pilar Salagre Carnero, Reus (ES); Marc Serra Queralt, Tarragona (ES); Pedro Uriz Sola, Tarragona (ES)

(73) Assignee: Repsol Quimica, S.A., Madrid (ES)

( * ) Notice: Subject to any disclaimer, the term of this patent is extended or adjusted under 35 U.S.C. 154(b) by 0 days.

(21) Appl. No.: 09/871,588

(22) Filed: May 31, 2001

(65) Prior Publication Data

US 2002/0016496 A1 Feb. 7, 2002

(30) Foreign Application Priority Data

Jun. 1, 2000 (ES) .......................................... 200001396

(51) Int. Cl.$^7$ .............................................. C07C 263/04
(52) U.S. Cl. ...................................................... 560/345
(58) Field of Search .......................................... 560/345

(56) References Cited

U.S. PATENT DOCUMENTS

| 4,572,804 | A | * | 2/1986 | Mullins |
| 5,326,903 | A | * | 7/1994 | Shimasaki et al. |
| 5,449,817 | A | * | 9/1995 | Jensen |
| 5,693,215 | A | * | 12/1997 | Zones |

* cited by examiner

Primary Examiner—Samuel Barts
(74) Attorney, Agent, or Firm—Ladas & Parry

(57) ABSTRACT

The procedure consists of the catalytic thermal decomposition of a carbamate in the presence of natural or synthetic carbamates as catalysts. Isocyanates with high yields and high reaction speeds are formed selectively.

42 Claims, No Drawings

ISOCYANATE PRODUCTION PROCEDURE

FIELD OF THE INVENTION

This invention refers to a procedure to produce isocyanates through the catalytic thermal decomposition of carbamates.

BACKGROUND OF THE INVENTION

Isocyanates are compounds with one or more —NCO functional groups, appropriate as raw materials widely used to produce polyurethanes, polyureas, etc., which are manufactured industrially on a large scale.

Isocyanates are mainly produced industrially from the reaction of amines with phosgene. However, the procedures that use phosgene have handling problems, since it is a highly toxic product, hydrogen chloride is produced as a by-product in large quantities and the use of highly sophisticated materials is required to avoid corrosion. This is why the industry is attempting to develop efficient isocyanate production procedures that avoid the use of phosgene as raw material.

One of these procedures is based on the thermal decomposition of carbamates. It is known that isocyanates can be obtained by heating liquid carbamates without catalysts (JP 1135753 A, U.S. Pat. No. 5,789,614). However, without catalysts, the speed of the thermal decomposition is generally limited and when the temperature is raised to speed up reaction time, by-products with high molecular weight are formed and yield tends to fall.

The use of several catalysts has been suggested in order to increase reaction speed and reduce the forming of by-products. Recommendations have been made to use elements from zinc, copper, aluminium, titanium and carbon groups (except carbon) and their oxides (JP 57158747 A), rare earths, antimony or bismuth and their oxides (JP 57159751 A), boron and derivatives of arsenic, antimony and quaternary ammonium salts (JP 57158746 A), synthetic boron, aluminium, silicon, tin, lead, antimony, zinc, yttrium, lanthanum, titanium, zirconium, niobium, wolfram or iron oxides (U.S. Pat. No. 5,326,903). All these procedures to produce isocyanates through the catalytic thermal decomposition of carbamates have the disadvantage associated to the forming of heavy by-products with high boiling points and slow reaction speeds. The application for European patent EP 672653 suggests a procedure to produce isocyanates through the thermal decomposition of carbamates in the presence of sulphonic acids or their alkaline metal salts. Although this patent application mentions high reaction speeds and high isocyanate yields, the catalysts used are not soluble in the reaction media and the separation or elimination of the a products of this reaction is difficult and costly.

COMPENDIUM OF THE INVENTION

The invention faces the problem of developing a procedure for the industrial manufacture of isocyanates. The solution provided by this invention is based on the catalytic thermal decomposition of the relevant carbamates using natural or synthetic silicates as catalysts.

One purpose of this invention, therefore, is a procedure for the production of isocyanates, through the catalytic thermal decomposition of the relevant carbamates, using natural or synthetic silicates as catalysts.

The procedure provided by this invention is a simple and economic process which obtains isocyanates with a small number of by-products with a high molecular weight, and high reaction speed, selectivity and yield, using low-cost catalysts which are easily separated from the reaction media by conventional methods, such as filtration or centrifuging, which lead to a simple and economic purification process for the isocyanates.

DETAILED DESCRIPTION OF THE INVENTION

The invention provides a procedure to produce isocyanates from carbamates by catalytic thermal decomposition, from here on the invention procedure, characterised in that it uses natural or synthetic silicates as catalysts.

In the sense used in this description, the term "isocyanate" includes all compounds that include at least one —NCO functional group. The isocyanates that can be obtained by the invention procedure include mono-, di- and polyisocyanates.

The carbamates that can be used in the invention procedure are compounds that include at least one —NHCOO— functional group, and can include saturated or unsaturated aliphatic groups, allylcyclical groups or aromatic groups. In a particular embodiment, the carbamates than can be used as raw material in the invention procedure correspond to the general formula:

$$R^1\text{—}(NHCOOR^2)_n$$

wherein $R^1$ and $R^2$, independently, identical or different, represent alkylic groups, alkylidene, alkenyl, allylcyclical groups, di-radicalic allylcyclical groups, aromatic groups, arylalkylic groups or di-radicalic aromatic groups; n is a whole number equal to 1, 2, 3 or 4.

The alkylic groups include methyl, ethyl, propyl, butyl, pentyl, hexyl, acryloyloxyethyl, 2-(methacryloyloxy)-ethyl, 2-dimethylamineoethyl, 3-dimethylamine-n-propyl, 2-methoxyethyl, 3-methoxybutyl groups, etc. The alkylidene groups include divalent acyclical groups such as the ethylidene, propylidene, butylidene, pentamethylene, hexamethylene groups, etc. The alkenyl groups include the propoenyl, butenyl, pentenyl groups, etc. The allylcyclical groups include the cyclopentyl, cyclohexyl, and cyclooctyl groups, etc. The di-radicalic allylcyclical groups are bivalent allylcyclical groups such as the 1,4-cyclohexylidene group. The aromatic and arylalkylic groups include the phenyl, tolyl, xylyl, naphthyl, biphenyl, anthanyl groups, etc. The di-radicalic aromatic groups are bivalent aromatic groups such as the 4,4'-methylen-bis-phenylene group. This list is not exhaustive, but merely informative.

These organic groups can contain other functional groups that are inert for isocyanates as substitutes, such as halogens, alcoxy, nitro, etc.

Examples of carbamates that can be used for the invention procedure include aliphatic carbamates such as 1,4-bis(methoxycarbonylamine)butane, 1,6-bis(methoxycarbonylamine)hexane, etc.; allylcyclical carbamates such as 1,3- or 1,4-bis(methoxycarbonylamine-methyl)benzene; 2,4'- or 4,4'-bis(methoxycarbonylamine)diphenylmethane, 4,4'-bis(methoxycarbonylamine)biphenyl, 1,5- or 2,6-bis(methoxycarbonylamine)naphthalene, etc.

The invention procedure can be carried out with a single carbamate or a mixture of 2 or more carbamates.

According to a particular embodiment of the invention procedure, the catalytic thermal decomposition of the carbamates is carried out in the presence of a solvent that is inert in the presence of isocyanates. The solvents that can be used in the invention procedure include aliphatic, allylcyclical and aromatic hydrocarbons, halogenated aromatic hydrocarbons, esters, ketones, ethers, etc. These solvents include alkanes such as hexane, decane, tetradecane, etc.; alicyclical hydrocarbons such as cyclohexane, cyclooctane, cyclododecane, decalin, etc.; aromatic hydrocarbons such as benzene, toluene, xylene, biphenyl, naphthalene, benzyltoluene, tetralin, pyrene, diphenyl-methane, triphenylmethane, phenylphthalene, etc.; esters such as dibutyl phthalate, dioctyl phthalate, diisodecyl phthalate, etc.; ketones such as methylethylcetone, aceto-phenone, etc.; and esters such as anisol, diphenylether, etc.

The quantity of solvent to be used is not critical and can vary between 0.05 and 100 times the weight of the carbamate used, preferably between 0.5 and 10 times its weight.

The temperature of the thermal decomposition of the carbamates is between 150° C. and 300° C., preferably between 200° C. and 275° C. When the reaction temperature is below 150° C., reaction time is very slow and inappropriate for an industrial process. Reaction temperatures over 300° C. are not preferred because undesirable quantities of by-products are formed.

Reaction can take place at reduced pressure or levels higher than atmospheric pressure. The choice of pressure basically depends on the solvent and reaction temperature selected. Reaction time is chosen depending on the kind of carbamate, solvent, reaction temperature and pressure and the type and quantity of the catalyst to be used. Any expert can select the best possible reaction conditions in each case by simple trials.

In the invention procedure, the carbamates are thermally decomposed to produce the relevant isocyanates and alcohols. To prevent these isocyanates from reacting with the alcohols to reproduce the original carbamates, it is recommended that the alcohols are removed from the reaction media as they are formed. This can easily be done by distilling when the alcohols formed have a low boiling point, such as methanol, ethanol, propanol, etc. To encourage the separation and extraction of the alcohols from the reaction media, inert gases can be circulated through the liquid reaction media, such as nitrogen, argon, methane, butane, etc., or inert solvents with a low boiling point can be added, such as benzene, hexane, etc.

The thermal decomposition reaction of the carbamates in accordance with the invention procedure can be carried out in a continuous or discontinuous process, preferably in continuous total mix shaken reactors, with the catalyst in powder form. Once the reaction is completed, the products, isocyanates, can be separated from the solid inorganic catalyst by simple operations such as filtration or centrifuging. The recovered catalyst can be re-used in later reactions, after being reactivated by known methods, for example by calcinating or washing with solvents. The reaction can also be carried out continuously feeding the carbamate solution to reactors with a fixed catalyst bed. This produces isocyanate solutions free from the catalyst which can be treated by known procedures to isolate very pure isocyanates.

The natural or synthetic silicates used as catalysts in the invention procedure are selected from natural or synthetic clays and zeolites. Clays can be broadly described as natural compounds, mainly of hydrated aluminum and silica, with a density between 2.5 and 2.7 g/ml, in which the proportions of silica, aluminum and water vary a great deal (Kingzett's Chemical Encyclopaedia, Ralph K. Strong Ed., Bailliere Tindall and Cox, 8$^{th}$ Edition, 1953, p. 228). The clay group includes minerals such as kaolins, bentonites, Fuller's earth, montmorillonites, etc. The clays preferred as catalysts for the invention are montmorillonites, laminar aluminosilicates from the group of the esmectites, with the structural formula $M^{n+}$ x/n-y$H_2O(Al_{4-x}Mg_x)o(Si_8)_t(O)_{20}(OH)_4$, where the $Al^{3+}$ and $Mg^{2+}$ cations occupy octahedral positions and $Si^{4+}$ occupies tetrahedral positions. $M^{n+}$ cations, generally $Na^+$, $K^+$, $Li^+$ and $Ca^{2+}$, are in interlaminar positions. Moreover, the preferred catalysts for the invention procedure are modified bentonites in their $H^+$ form.

The natural or synthetic zeolites that are adequate as catalysts for the invention procedure are crystalline aluminosilicates made up of $SiO_4$ and $AlO_4$ tetrahedrons that can contain other cations, such as $B^{3+}$, $Ga^{3+}$, $Cr^{3+}$, $Fe^{3+}$, $Zn^{2+}$, $Ti^{4+}$, etc., in isomorphic substitution.

Examples of zeolites that can be used for the invention procedure are ZSM;-5, TS-1, TS-2, ZSM-11, Line X, Linde Y, Faujesite and Mordenite.

The clays and zeolites that can be used as catalysts in the invention procedure can be previously modified by known processes, such as calcination, the creation of pillars, etc. They can also be pre-treated with inorganic acids such as chlorhidric acid, sulphuric acid, phosphoric acid, etc., and organic acids such as acetic acid, citric acid, p-toluensulphonic acid, etc. They can also be treated with ammonia or organic bases such as primary and secondary amines and tertiary amines such as quinoline, pyridines, etc., or with gases of the carbon dioxide type, etc. The treatments that are indicated to modify the clays and zeolites are well known and not the subject of this invention. These treatments are applied in order to modify the acid-base properties of the catalysts, to improve their activity and/or selectivity in the thermal decomposition reaction of the carbamates into isocyanates.

The following examples are particular embodiments of this invention and should not be considered as exhaustive, but merely informative.

EXAMPLE 1

In a 250-ml flask fitted with a cooling column, dissolve 100 mg of N-carbomethoxyanylin in 8 ml of 1,2-anhydrous dichlorobenzene and add 100 mg of montmorillonite of commercial origin (Fluka, catalogue number 69866). The reaction mix is shaken constantly for a maximum of 5 hours at the solvent reflux temperature. The methanol that is formed is extracted through the top of the cooling column. After this time, the reaction mix is left to cool at ambient temperature and filtered to separate the montmorillonite from the solution. The solvent is separated later by distilling and the conversion of N-carbomethoxyanylin into phenylisocyanate is quantified by $^1H$ (MNR $^1H$) Magnetic Nuclear Resonance, Gas Chromatography coupled to Mass Spectrometry (CG-MS), after the phenylisocyanate being transformed in situ into N-carbopropoxyanylin. The transformation of the phenylisocyanate into N-carbopropoxyanylin is carried out with 1-propanol in the presence of a base, DABCO (1,4-diazabiciclo-(2,2,2)octane), to obtain N-carbopropoxyanylin, which is analysed by gas chromatography since it elutes at retention times that are different enough from those of the original carbamate. The chromatography column used is Ultra-1 with 5% of diphenylmethylsilicone and 95% of dimethylsilicone. The conversion of N-carbomethoxyanylin into phenylsocyanate is 96% in 1 hour of reaction time.

EXAMPLE 2

Using the same quantities of reagents and catalyst and the same reaction conditions as in Example 1, the reaction is carried out replacing 1,2-dichlorobenzene by 1,3,4-trichlorobenzene, obtaining 86% of conversion into phenylisocyanate in 1 hour of reaction time.

EXAMPLE 3

The reaction and quantification procedure described in Example 1 is used, but with 100 mg of N-carbometoxy-(p-chloride)-anylin, 8 ml of 1,2-dichlorobenzene and 100 mg of montmorillonite of commercial origin (Fluka, catalogue number 69866). The conversion of the carbamate into p-chlorophenylisocyanate is 99% in 1 hour of reaction time.

EXAMPLE 4

Using the same quantities of reagents and catalyst and the same reaction conditions as in Example 3, but replacing the 1,2-dichlorobenzene by 1,3,4-trichlorobenzene, 96% conversion of the carbamate into p-chlorophenylisocyanate is obtained in 1 hour of reaction time.

EXAMPLE 5

The reaction and quantification procedure described in Example 1 is repeated, using 100 mg of N-carbomethoxynaphthylamin, 8 ml of 1,2-dichlorobenzene and 100 mg of montmorillonite of commercial origin (Fluka, catalogue number 69866). The conversion of the reaction into naphthylisocyanate is 93% in 5 hours of reaction time.

EXAMPLE 6

Using the same quantities of reagents and catalyst and the same reaction conditions as in Example 5, but replacing the 1,2-dichlorobenzene by 1,3,4-trichloroobenzene, 94% conversion of the carbamate into naphthylisocyanate is obtained in 1 hour of reaction time.

EXAMPLE 7

The reaction procedure described in Example 1 is repeated using 1,000 mg of 4,4'-methylen-bis(N-carbomethoxyanylin), 40 ml of decalin and 250 mg of montmorillonite of commercial origin (Fluka, catalogue number 69866).

The quantification of the reaction can be carried out using the MNR 1H technique directly on the diisocyanate, through the ratio of the intensity of the dicarbamate, diisocyanate and monoisocyanate signals.

After 24 hours of reaction time, the conversion of the carbamate into 4,4'-methylen-bis(phenylisocyanate) is 97% and into monoisocyanate 3%.

EXAMPLE 8

The reaction and quantification procedure described in Example 7 is repeated, using 1,000 mg of 4,4'-methylen-bis (N-carbomethoxyanylin), 80 ml of decalin and 250 mg of montmorillonite of commercial origin (Fluka, catalogue number 69866) previously treated with quinolin. The modification of the commercial montmorillonite with quinolin is carried out by the adsorption method.

After 24 hours of reaction time, the conversion into 4,4'-methylene-bis(phenylisocyanate) is 96% and into monoisocyanate 4%.

EXAMPLE 9

The reaction and quantification procedure described in Example 7 is repeated using 1,000 mg of 4,4'-methylen-bis (N-carbomethoxyanylin), 80 ml of decalin and 250 mg of commercial bentonite "Majorbenton B" (AEB Ibérica, S. A.), previously treated with ammonium nitrate. The modification of the bentonite is carried out by the thermal exchange and decomposition method.

After 24 hours of reaction time, the total conversion into isocyanates is 82%, the selectivity to 4,4'-methylenebis (phenylisocyanate) is 71% and to monoisocyanate is 29%.

EXAMPLE 10 (COMPARATIVE)

The reaction and quantification procedure described in Example 7 is repeated, using 1,000 mg of 4,4'-methylen-bis (N-carbomethoxyanylinn) and 80 ml of decalin, without a catalyst.

After 24 hours of reaction time, the total conversion into isocyanates is 44%, the selectivity to 4,4'-methylen-bis (phenylsocyanate) is 9% and to monoisocyanate 35%.

What is claimed is:

1. A procedure for producing isocyanates having multiple isocyanate groups from carbamates having multiple carbamate groups by catalytic thermal decomposition, wherein natural or synthetic silicates are used as catalysts.

2. The procedure as claimed in claim 1, wherein the natural silicates are clays.

3. The procedure as claimed in claim 1, wherein the natural or synthetic silicates are zeolites.

4. The procedure as claimed in claim 1 wherein the silicates are montmorillonites.

5. The procedure as claimed in claim 2, wherein the clays are modified bentonites in their $H^+$ form.

6. The procedure as claimed in claim 3, wherein the zeolites are selected from the group consisting of ZSM-5, TS-1, TS-2, ZSM-11, Linde X, Linde Y, Faujesite, Mordenite, and mixtures thereof.

7. The procedure as claimed in claim 1, wherein the natural or synthetic silicates are calcined before being used as the catalysts.

8. The procedure as claimed in claim 1, wherein the natural or synthetic silicates are treated with organic or inorganic acids before being used as the catalysts.

9. The procedure as claimed in claim 1, wherein the natural or synthetic silicates are treated with ammonia or with organic bases before being used as the catalysts.

10. The procedure as claimed in claim 1, wherein the catalytic thermal decomposition occurs at a temperature between 150° C. and 300° C.

11. A procedure as claimed in claim 1, wherein the catalytic thermal decomposition occurs at a temperature between 200° C. and 275° C.

12. A procedure as claimed in claim 1, wherein the carbamate comprises a mixture of two different carbamates.

13. A process for converting a carbamate having multiple carbamate groups into an isocyanate having multiple isocyanate groups, wherein the process comprises the steps of:

(1) providing the carbamate, wherein the carbamate has a formula I $$R^1-(NHCOOR^2)_n \qquad \text{(formula I)}$$

wherein $R^1$ and $R^2$ are the same or different than each other, wherein $R^1$ and $R^2$ are each independently an organic group selected from the group consisting of alkyl groups, alkylidene groups, alkenyl groups, allylcyclical groups, di-radical allylcyclical groups, aromatic groups, arylalkyl groups, and di-radical aromatic groups, wherein the organic group optionally contains a halogen, an alkoxy group, or a nitro group; and wherein n equals 2, 3, or 4;

(2) providing a catalyst, wherein the catalyst comprises a natural or synthetic silicate; and (3) contacting the catalyst with the carbamate, wherein the isocyanate having the multiple isocyanate groups is produced by catalytic thermal decomposition.

14. The process as claimed in claim 13, wherein the organic group is selected from the group consisting of a methyl group, an ethyl group, propyl groups, butyl groups, pentyl groups, hexyl groups, an acryloyloxyethyl group, a 2-(methacryloyloxy)-ethyl group, a 2-dimethoxyaminoethyl group, a 3-dimethylamine-n-propyl group, a 2-methoxyethyl group, 3-methoxybutyl group, an ethylidene group, a propylidene group, a butylidene group, a pentamethylene group, a hexamethylene group, a propoenyl group, a butenyl group, a pentenyl group, a cyclopentyl group, a cyclohexyl group, a cyclooctyl group, a 1,4-cyclohexylidene group, a phenyl group, a tolyl group, a xylyl group, a naphtyl group, a biphenyl group, an anthanyl group, and a 4-4'methylen-bis-phenylene group.

15. The process as claimed in claim 13, wherein the isocyanate having the multiple isocyanate groups has a formula II

$R^1$—(NCO)$_n$                           (formula II)

wherein $R^1$ and n in the formula II are defined in claim 13, and wherein $R^1$ in the formula I and in the formula II is saturated.

16. The process as claimed in claim 13, wherein the isocyanate having the multiple isocyanate groups has a formula II

$R^1$—(NCO)$_n$                           (formula II)

wherein $R^1$ and n in the formula II are defined in claim 13, and wherein $R^1$ in the formula I and in the formula II is unsaturated.

17. The process as claimed in claim 13, wherein before step (3) the catalyst is calcined.

18. The process as claimed in claim 13, wherein before step (3) the catalyst is treated with an inorganic or organic acid.

19. The process as claimed in claim 13, wherein the silicate comprises a clay.

20. The process as claimed in claim 13, wherein the silicate comprises a zeolite.

21. The process as claimed in claim 13, wherein the silicate comprises a montmorillonite.

22. The process as claimed in claim 13, wherein the silicate comprises a modified bentonite in an H$^+$ form.

23. The process as claimed in claim 20, wherein the zeolite is selected from the group consisting of ZSM-5, TS-1, TS-2, ZSM-11, Linde X, Linde Y, Faujesite, Mordenite, and mixtures thereof.

24. The process as claimed in claim 13, wherein before step (3) the silicate is treated with ammonia or an organic base.

25. The process as claimed in claim 13, wherein the catalytic thermal decomposition occurs at a temperature between 150° C. and 300° C.

26. The process as claimed in claim 15, wherein the silicate comprises montmorillonite.

27. The process as claimed in claim 16, wherein the silicate comprises montmorillonite.

28. The process as claimed in claim 13, wherein in step (3), the carbamate comprises a mixture of two different carabamates.

29. The process as claimed in claim 26, wherein in step (3), the carbamate comprises a mixture of two different carabamates.

30. The process as claimed in claim 27, wherein in step (3), the carbamate comprises a mixture of two different carabamates.

31. The process as claimed in claim 13, wherein the catalytic thermal decomposition occurs at between 200° C. and 275° C.

32. A process for producing an isocyanate from a carbamate by catalytic thermal decomposition using a catalyst, wherein the catalyst comprises montmorillonite.

33. The process as claimed in claim 32, wherein the isocyanate is a monoisocyanate, and wherein the carbamate is a monocarbamate.

34. The process as claimed in claim 32, wherein the carbamate has a formula I

$R^1$—(NHCOOR$^2$)$_n$                           (formula I)

wherein $R^1$ is an aromatic group, wherein $R_2$ is an alkyl group, and wherein n equals 1.

35. The process as claimed in claim 34, wherein $R^1$ is a phenyl group, and wherein $R^2$ is a methyl group.

36. A process for converting a mixture of two carbamates into two isocyanates, wherein the process comprises the steps of:

(1) providing a mixture of a first carbamate and a second carbamate, wherein the first carbamate and the second carbamate each independently have a formula I

$R^1$—(NHCOOR$^2$)$_n$                           (formula I)

wherein $R^1$ and $R^2$ are the same or different than each other, wherein $R^1$ and $R^2$ are each independently an organic group selected from the group consisting of alkyl groups, alkylidene groups, alkenyl groups, allylcyclical groups, di-radical allylcyclical groups, aromatic groups, arylalkyl groups, and di-radical aromatic groups, wherein the organic group optionally contains a halogen, an alkoxy group, or a nitro group;

wherein n equals 1, 2, 3, or 4; and wherein the first carbamate is different than the second carbamate;

(2) providing a catalyst, wherein the catalyst comprises a natural or synthetic silicate; and (3) contacting the catalyst with the mixture of the first carbamate and the second carbamate, wherein a first isocyanate is produced from the first carbamate by catalytic thermal decomposition; wherein a second isocyanate is produced from the second carbamate by the catalytic thermal decomposition; and wherein the first isocyanate is different than the second isocyanate.

37. The process as claimed in claim 36, wherein after step (3) the first isocyanate is isolated and the second isocyanate is isolated.

38. The process as claimed in claim 13, wherein the catalyst is selected from the group consisting of: (1) laminar aluminosilicates selected from the group consisting of esmectites; and (2) crystalline aluminosilicates having SiO$_4$ and AlO$_4$ tetrahedrons, wherein the tetrahedrons optionally contain B$^{3+}$, Ga$^{3+}$, Cr$^{3+}$, Fe$^{3+}$, Zn$^{2+}$, and Ti$^{4+}$ cations in isomorphic substitution.

39. A process as claimed in claim 13, wherein $R^1$ is not a methyl group; and wherein in the formula I two carbamate groups are not bonded to the same carbon atom.

40. A process as claimed in claim 15, wherein $R^1$ is not a methyl group; and wherein in the formula I two carbamate groups are not bonded to the same carbon atom.

41. A process as claimed in claim 16, wherein $R^1$ is not a methyl group; and wherein in the formula I two carbamate groups are not bonded to the same carbon atom.

42. A process as claimed in claim 13, wherein after step (3) the isocyanate having the multiple isocyanate groups is isolated.

\* \* \* \* \*